US008343506B2

(12) United States Patent
Frolov et al.

(10) Patent No.: US 8,343,506 B2
(45) Date of Patent: Jan. 1, 2013

(54) CHIMERIC CHIKUNGUNYA VIRUS AND USES THEREOF

(75) Inventors: Ilya V. Frolov, Birmingham, AL (US); Scott C. Weaver, Galveston, TX (US); Eryu Wang, Houston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 154 days.

(21) Appl. No.: 12/798,796

(22) Filed: Apr. 12, 2010

(65) Prior Publication Data

US 2011/0171249 A1   Jul. 14, 2011

Related U.S. Application Data

(63) Continuation-in-part of application No. PCT/US2008/011706, filed on Apr. 11, 2008.

(60) Provisional application No. 60/998,548, filed on Oct. 11, 2007.

(51) Int. Cl.
*A61K 39/12* (2006.01)
*C12N 7/01* (2006.01)
*C12N 15/86* (2006.01)
*C12Q 1/70* (2006.01)

(52) U.S. Cl. ... 424/199.1; 424/218.1; 435/5; 435/235.1; 435/320.1; 536/23.72

(58) Field of Classification Search ........................ None
See application file for complete search history.

(56) References Cited

U.S. PATENT DOCUMENTS

| | | | |
|---|---|---|---|
| 6,168,923 B1 | 1/2001 | Scott et al. | |
| 6,261,570 B1 * | 7/2001 | Parker et al. | 424/205.1 |
| 6,296,854 B1 * | 10/2001 | Pushko et al. | 424/218.1 |
| 2003/0148262 A1 * | 8/2003 | Polo et al. | 435/5 |
| 2004/0253271 A1 * | 12/2004 | Platteborze et al. | 424/199.1 |
| 2005/0266550 A1 * | 12/2005 | Rayner et al. | 435/320.1 |
| 2010/0233209 A1 * | 9/2010 | Higgs et al. | 424/218.1 |

OTHER PUBLICATIONS

Vanlandingham et al (American Journal of Tropical Medicine and Hygiene 74:663-669, Apr. 2006).*
Edelman et al (American Journal of Tropical Medicine and Hygiene 62:681-685, 2000).*
Ni et al (American Journal of Tropical Medicine and Hygiene 76:774-781, 2007).*
Perri et al (Journal of Virology 77:10394-10403, 2003).*
Gorchakov et al (Virology 366:212-225, 2007).*
Vanlandingham, D.L., et al., Determinants of Vector Specificity of O'Nyong Nyong and Chikungunya Viruses in Anopheles and Aedes mosquitoes', Am. J. Trop. Med. Hyg., 2006, pp. 663-669, vol. 74 No. 4.
Wang, E., et al., "Chimeric Alphavirus Vaccine Candidates for Chikungunya", Vaccine, Aug. 8, 2008, pp. 5030-5039, vol. 26.
International Search Report, PCT/US2008/011716, date of ISR Apr. 8, 2009.

* cited by examiner

*Primary Examiner* — Mary E Mosher

(57) ABSTRACT

The present invention discloses a chimeric Chikungunya virus comprising a heterologous alphavirus cDNA fragment and a Chikungunya virus cDNA fragment. The heterologous alphavirus may include but is not limited to Sindbis virus, Eastern equine encephalitis virus or Venezuelan equine encephalitis virus. The present invention also discloses the use of this chimeric Chikungunya virus as vaccines and in serological and diagnostic assays.

15 Claims, 10 Drawing Sheets

CHIMERIC CHIKUNGUNYA VIRUS AND USES THEREOF

CROSS-REFERENCE TO RELATED APPLICATIONS

This is a continuation-in-part application which claims benefit of priority under 35 U.S.C. §120 of international application PCT/US2008/011706, filed Apr. 11, 2008, which claims benefit of priority under 35 U.S.C. §119(e) of provisional application U.S. Ser. No. 60/998,548, filed Oct. 11, 2007, the entirety of both of which are hereby incorporated by reference.

This invention was made with government support under U54AI057156 awarded by the National Institute of Allergy and Infectious Disease. The government has certain rights in the invention.

BACKGROUND OF THE INVENTION

1. Field of the Invention

The present invention relates to the fields of molecular biology, virology and immunology. More specifically, the present invention provides an attenuated recombinant chimeric chikungunya virus (CHIKV) and discloses its use as vaccines and in serological and diagnostic assays.

2. Description of the Related Art

Chikungunya virus has for decades been an important etiologic agent of human disease in Africa and Asia. However, cases are grossly underestimated because Chikungunya virus infections usually cannot be distinguished clinically from dengue. Recently, Chikungunya virus caused epidemics involving millions of people on islands off the eastern coast of Africa that are popular destinations for European tourists (Schuffenecker et al., 2006), as well as in the Indian subcontinent (Charrel et al., 2007; Kalantri et al., 2006). Further, unlike past epidemics that were usually associated with *Aedes aegypti* transmission, *Ae. albopictus* was implicated as the principal mosquito vector in the recent Indian Ocean outbreaks.

Typically, Chikungunya virus causes a severely incapacitating, self-limited disease characterized by fever, rash and severe joint pains: the latter can persist for months. Notably, the recent Indian Ocean outbreaks included many fatal cases, raising the possibility that Chikungunya virus has become more virulent. Chikungunya virus may spread into Western Hemisphere through the movement of infected travelers from Asia and Africa (Charrel et al., 2007) or through introduction of infected mosquitoes carried from epidemic sites in shipping containers. The dramatic spread since 1980 of dengue viruses throughout tropical America, via the same vectors and human hosts, serves as a precedent. If introduced into the New World, Chikungunya virus could cause millions of additional cases of severe and possibly fatal disease.

In addition to its enormous potential as an emerging virus, Chikungunya virus is also underestimated as a potential biological weapon. The 39 documented laboratory infections reported by U.S. Department of Health and Human Services in 1981 strongly suggest that Chikungunya virus is infectious via aerosol route. Chikungunya virus was being weaponized by the United States army when the offensive program was terminated and is considered as a biological weapon by the German and Australian governments.

In general, alphaviruses have plus sense RNA genomes of approximately 11.5 kB that encode 4 nonstructural (nsP1-4) and 3 structural proteins (capsid, E1 and E2 glycoproteins encoded by subgenomic 26S mRNA). The terminal untranslated genome regions (UTR) include repeated sequence elements near the 3' end that are critical for replication in mosquito cells (Kuhn et al, 1996; Kuhn et al., 1992). Alphaviruses enter cells via receptor-mediated endocytosis (Kielian and Helenius, 1986). The high affinity laminin receptor serves as a mammalian and mosquito cell (in vitro) receptor for Sindbis virus (SINV) (Wang et al., 1992) and VEEV (Ludwig et al., 1996), while other protein receptors for SINV have been identified in mouse neural (Ubol and Griffin, 1991) and chicken cells (Wang et al., 1991). C-type lectins (DC-SIGN, L-SIGN) can function as receptors for infection of dendritic cells (Klimstra et al., 2003).

Following passage in cell culture, alphaviruses adapt to bind to heparan sulfate, which is usually accompanied by attenuation in vivo (Bernard et al., 2000; Byrnes and Griffin, 1998; Byrnes and Griffin, 2000; Klimstra et al., 1998). Genomic RNA is translated by cellular components into a nonstructural polyprotein and is the template for minus-strand RNA synthesis involving nonstructural proteins (nsPs) (Strauss and Straus, 1994). The 26S mRNA is translated as a polyprotein; the capsid protein is cleaved in the cytoplasm and the remaining polyprotein is processed in the secretory pathway to yield the E1 and E2 glycoproteins, which are inserted into the plasma membrane. Following encapsidation of genomic RNA, 70 nm enveloped virions mature when nucleocapsids bud through the plasma membrane (Schlessinger and Schlessinger, 1996; Strauss and Strauss, 1994).

Most alphaviruses replicate in and cause extensive cytopathic effects (CPE) in vertebrate cells in vitro, but infection of mosquito cells usually leads to persistent infection not usually accompanied by cytopathic effects. The mechanisms of alphavirus cytopathogenicity are not fully understood. However, the suppression of host cell gene expression, which allows alphaviruses to compete with cellular metabolism for their replication, is an important component. The alphavirus components responsible for shutdown of cellular gene expression have recently been identified for several members of the genus; Old World viruses SINV (Frolova et al., 2002) and Semliki Forest (Garmashova et al., 2007) use their nsP2 for transcriptional shutoff. However, the New World alphaviruses Eastern (EEEV) (Aguilar et al., 2007) and Venezuelan equine encephalitis (VEEV) (Garmashova et al., 2007) rely on their capsid protein rather than on nsP2. The ability of these capsid proteins to inhibit cellular transcription appears to be controlled by the amino-terminal domain rather than by their protease activity or by their positively charged RNA-binding domains.

Despite their importance as emerging viruses and potential biological weapons, there are no licensed vaccines or therapeutics for alphaviruses. Several experimental human and licensed veterinary vaccines have been produced by inactivation of wild-type or attenuated alphaviruses, but all are poorly immunogenic and require multiple vaccinations and frequent boosters (Tsai et al., 2002). Attenuated strains of Venezuelan equine encephalitis virus (VEEV) (Berge et al., 1961) and Chikungunya virus (Levitt et al., 1986) were developed by cell culture passages of virulent, wild-type strains. The VEEV vaccine, TC-83, has been tested extensively in humans and exhibit high rates of reactogenicity and many people failed to seroconvert (Pittman et al., 1996).

The Chikungunya virus vaccine is attenuated and immunogenic in mice and Rhesus macaques, although these monkeys develop viremia after vaccination (Levitt et al., 1986). The vaccine is also highly immunogenic in humans (Edelman et al., 2000). However, 5 of 59 human vaccines developed transient arthralgia during phase II safety studies. Although the mechanism of reactogenicity for the Venezuelan equine encephalitis virus and Chikungunya virus vaccine strains has not been determined, it is likely that the reversions of attenuating point mutations occur. TC-83, developed by 83 serial cell culture passages has only 2 attenuating mutations (Kinney et al., 1993). The Chikungunya virus vaccine strain, which was developed with only 18 passages probably has similar if not lower number of attenuating mutations. Thus, alphavirus vaccine strains with attenuating point mutations are not stable.

Despite its importance as an emerging arboviral disease and its potential as a biological weapon, the prior art is deficient in safety and immunogenic compositions effective as vaccines that can be used to prevent an individual from infection caused by Chikungunya virus. The present invention fulfills this long-standing need and desire in the art.

SUMMARY OF THE INVENTION

In one embodiment of the present invention, there is provided an isolated nucleic acid encoding a chimeric Chikungunya virus. Such a nucleic acid comprises Venezuelan equine encephalitis and eastern equine encephalitis cDNA fragment and the Chikungunya virus cDNA fragment. VEEV and EEEV fragments include the nonstructural genes which were shown to have no effect on the cellular transcription and translation. The Chikungunya cDNA fragment encodes the structural viral genes that have been shown to have no effect on cellular transcription and translation. Thus, in contrast to nonchimeric VEEV, EEEV and CHIKV, the chimeric viruses are incapable of interfering with the induction of the antiviral response and demonstrate highly attenuated phenotype and do not develop profound cytopathic effects in cultured cells.

In a further related embodiment of the present invention, there is provided a vector comprising the nucleic acid described herein, a host cell comprising and expressing the vector and an attenuated chimeric Chikungunya virus comprising the DNA described herein.

In yet another related embodiment of the present invention, there is provided a pharmaceutical composition comprising the above-mentioned attenuated Chikungunya virus and a pharmaceutically acceptable carrier.

In a related embodiment of the present invention, there is provided an immunogenic composition comprising a live attenuated chimeric Chikungunya virus described herein.

In another related embodiment of the present invention, there is provided a method of protecting an individual from infections resulting from exposure to Chikungunya virus. Such a method comprises administering an immunologically effective amount of the immunogenic composition comprising the live attenuated chimeric Chikungunya virus described herein, where the composition elicits an immune response against the Chikungunya virus in the individual, thereby protecting the individual from the infection.

In a further related embodiment of the present invention, there is provided an immunogenic composition comprising an inactivated chimeric Chikungunya virus, where the virus comprises the attenuated chimeric Chikungunya virus described herein that is inactivated.

In yet another embodiment of the present invention, there is provided a method of protecting an individual from infections resulting from exposure to Chikungunya virus. This method comprises administering an immunologically effective amount of the immunogenic composition comprising the inactivated chimeric Chikungunya virus described herein, where the composition elicits an immune response against the Chikungunya virus in the individual, thereby protecting the individual from the infection.

In still yet another embodiment of the present invention, there is provided a method of determining the presence of an antibody to Chikungunya virus in a subject. Such a method comprises obtaining a serum sample from the subject and performing an assay using the attenuated chimeric Chikungunya virus described herein to determine the presence or absence of antigenic reactions, the effect of physical properties of the Chikungunya virus or a combination thereof in the serum sample, thereby determining the presence of the antibody to Chikungunya virus in the subject.

In another embodiment of the present invention, there is provided a method of determining the presence of an antibody to Chikungunya virus in a subject. This method comprises obtaining serum sample from the subject and performing assay using an inactivated chimeric Chikungunya virus, where the inactivated chimeric Chikungunya virus comprises the attenuated chimeric Chikungunya virus described herein that is inactivated to determine presence or absence of antigenic reactions, effect of physical properties of the western equine encephalitis virus or a combination thereof in the serum sample, thereby determining the presence of the antibody to Chikungunya virus in the subject.

In yet another embodiment of the present invention, there is provided a kit. Such a kit comprises the attenuated chimeric Chikungunya virus described herein, the attenuated chimeric Chikungunya virus described herein that is inactivated or combinations thereof.

BRIEF DESCRIPTION OF THE DRAWINGS

FIG. 1 shows a diagram of the genetic composition of the chimeric CHIKV vaccine candidates and the specific infectivities of transcribed RNAs following electroporation of BHK cells. nsP1-4, nonstructural proteins 1-4; SG, subgenomic promoter; C, capsid; E1 and E2, envelope glycoproteins 1 and 2.

FIG. 2 shows body weights in vaccinated or sham-vaccinated C57BU6 mice after intranasal (IN) challenge with $1.8 \times 10^7$ PFU of the Ross strain of Chikungunya virus.

FIG. 5 shows body weights in 3-week-old female C57BL/6 mice after SC vaccination with EEE/CHIKV, TC-83/CHIKV or SIN/CHIKV at doses of 5.8, 5.6 and 5.8 $\log_{10}$ PFU/mouse, respectively, or of 3-week-old female NIH Swiss mice after SC vaccination with EEE/CHIKV, TC-83/CHIKV or SIN/CHIKV at doses of 5.8, 5.6 and 5.8 $\log_{10}$ PFU/mouse, respectively.

FIGS. 7A-7C show replication of CHIKV chimeric vaccine candidates or the wt LR CHIKV strain after SC infection of 3-4-day-old NIH Swiss mice with ca. $10^5$ PFU. The limits of detection are indicated by the dashed lines.

FIG. 8 shows body weight of vaccinated and sham-vaccinated mice after CHIKV challenge. Cohorts of five 3-week-old females were vaccinated with EEE/CHIKV, TC-83/CHIKV or SIN/CHIKV at doses of 5.3-5.8 $\log_{10}$ PFU/mouse. Three weeks later, the mice were challenged with the Ross strain of CHIKV IN at a dose 6.5 $\log_{10}$ PFU.

DETAILED DESCRIPTION OF THE INVENTION

Figure 3:
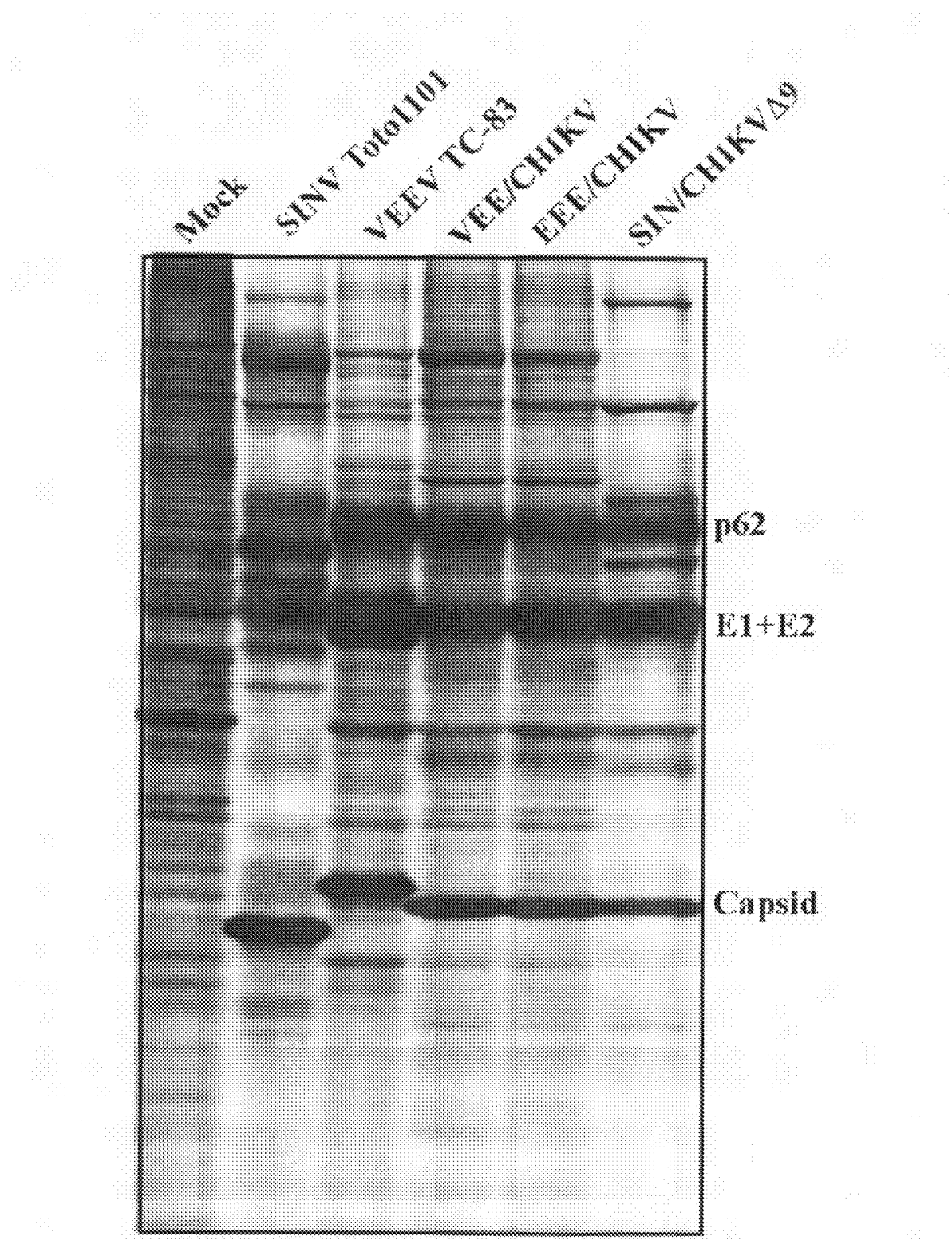
FIG. 3 shows the expression of structural proteins by chimeric vaccine candidates. BHK-21 cells were infected with SINV Toto1101, VEEV TC-83, VEE/CHIKV, EEE/CHIKV and SIN/CHIKVD9 at an MOI of 20 PFU/cell. At 16 h post infection, cells were washed three times with PBS and incubated for 1 h at 37° C. in DMEM lacking methionine and supplemented with 0.1% FBS and 20 mCi/ml of [$^{35}$S]methionine. After this incubation, cells were scraped into PBS, pelleted by centrifugation and dissolved in standard gel-loading buffer. Equal amounts of proteins were loaded onto sodium dodecyl sulfate (SDS)-10% polyacrylamide gels. Markers indicate p62, E1+E2 (envelope glycoproteins E1 and E2), and capsid.
Figure 4A:
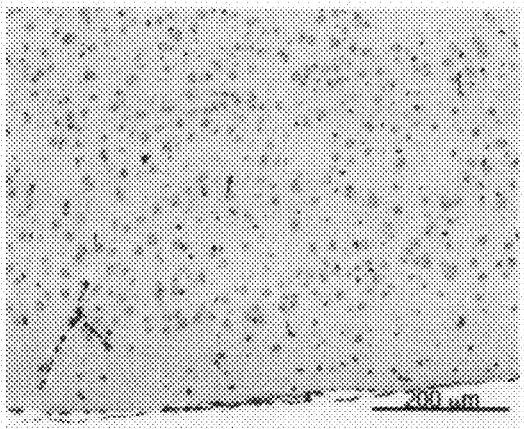
FIG. 4A-4D show the histopathology and immunohistochemistry of 5-week-old C57/BL6 mouse brains following IN infection with the Ross strain of CHIKV. H&E staining of mouse brains at day 7 after IN infection with either PBS (FIG. 4A) or CHIKV (FIG. 4B). CHIKV-infected mice showed severe, multifocal inflammation and liquefactive necrosis in the cerebral cortex. Perivascular cuffs were also located diffusely throughout the cerebral cortex (arrow). Immunohistochemical staining of the cerebral cortex at day 7 after IN infection with CHIKV (FIGS. 4C, 4D). Primary antibodies against Modoc virus (MODV) were used as a negative control (FIG. 4C). Using primary antibodies against CHIKV, there was intense positive staining (dark red) of degenerating neurons located in the necrotic areas of the cerebral cortex (FIG. 4D).
Figure 4B:
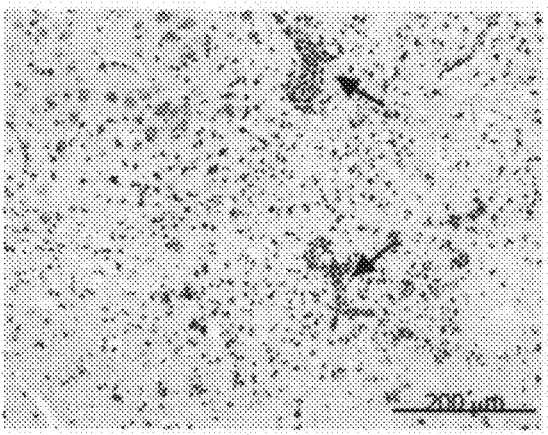
Figure 4C:
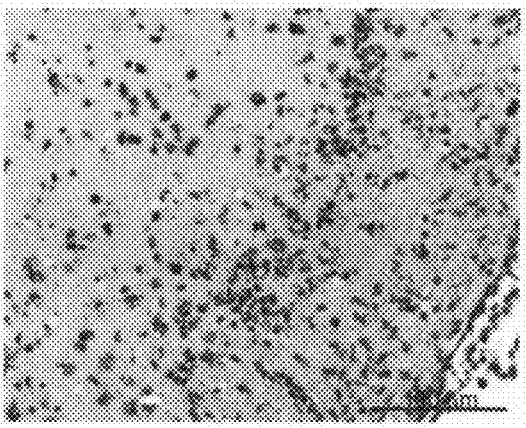
Figure 4D:
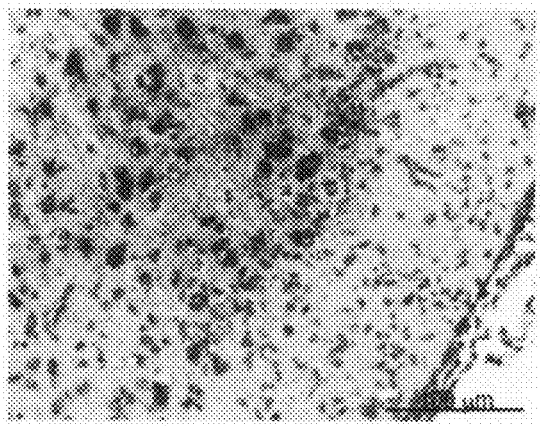

The present invention is drawn to immunogenic compositions comprising chimeric chikungunya virus that can be used in the treatment prevention of infections caused by Chikungunya virus. Additionally, these immunogenic compositions can also be used to provide immunoprotection against infections caused by Chikungunya virus. Furthermore, they can also be used in diagnostic assays. The chimeric alphaviruses disclosed herein are generated using a strategy that is different from previously described Chikungunya virus strains. For instance, they use heterologous alphavirus-derived backbone and cis-acting elements. These chimeric alphavirus strains are identical in their structural protein content to wild type Chikungunya virus, yet are highly attenuated due to exclusion of any viral proteins (VEEV and EEEEV capsid and CHIKV nsP2) that can inhibit the antiviral response in the virus-infected cells and thus, more safer and more effective than live-attenuated vaccine strains, as safer strains to produce formalin-inactivated vaccines and as safer diagnostic reagents for serological assays. In contrast to parental VEEV, EEEV and CHIKV, the chimeric viruses require biosafety level 2, but not biosafety level 3 biocontainment conditions for large-scale propagation and purification. Thus, the chimeric Chikungunya virus disclosed herein are novel.

Infectious cDNA clones encoding chimeric alphaviruses were developed for use as live attenuated vaccine strains and as diagnostic reagents. These strains include the cis-acting sequences from the 5' and 3' termini of the eastern equine encephalitis virus or Venezuelan equine encephalitis virus genome as well as the 26S promoter and non-structural protein genes. The structural protein genes were derived from Chikungunya virus. These recombinant chimeric viruses were highly attenuated in the mouse model for Chikungunya disease and can generate immunity that protects them against infections resulting from natural exposure of from a bioterror attack. The present invention contemplates optimizing and testing the Chikungunya virus vaccines in murine models for virulence, immunogenicity, efficacy (including against O'nyong-nyong virus) and environmental safety.

Additionally, the present invention also contemplates optimizing vaccine formulations to improve thermal stability and testing the most promising vaccine candidates of immunogenicity and efficacy as well as virulence in Rhesus macaques. The most promising vaccine candidates are also tested for safety in GLP histopathology/toxicology studies and neurovirulance studies. In addition to their use as vaccines, the chimeric Chikungunya virus may also be used as surrogates for wild type Chikungunya virus in serological, diagnostic assays and for production of formalin-inactivated vaccines. Additionally, since they are highly attenuated and can be handled at biosafety level 2, the use of these surrogates will dramatically improve efficiency and safety in the diagnostic laboratories and vaccine production facilities.

Thus, the narrowest application of the present invention is its use as a live-attenuated vaccine in humans. Broader applications include any experiments or assays that measure antigenic reactions or other physical properties of Chikungunya virus particles since the chimeric Chikungunya virus has the same protein makeup and structure as wild type Chikungunya virus. These include but are not limited to serological assays such as plaque reduction neutralization tests, enzyme linked immunosorbent assays, hemagglutination inhibition and complement fixation assays conducted with live or inactivated antigens produced from the chimeras, production of virus for inactivation using formalin for vaccination of humans or animals and structural studies employing methods such as electron microscopy.

The present invention is directed to a DNA encoding a chimeric Chikungunya virus comprising a heterologous alphavirus cDNA fragment and the Chikungunya virus cDNA fragment. Specifically, the heterologous VEEV and EEEV, cDNA fragment comprises cis-acting sequences from the 5' and 3' termini, 26S promoter and nonstructural protein genes while the Chikungunya virus cDNA fragment comprises structural protein genes and the 5' untranslated region of the subgenomic message. The heterologous alphavirus may include Sindbis virus, Eastern equine encephalitis virus or Venezuelan equine encephalitis virus. Representative examples of the Eastern equine encephalitis virus are BeAr436087 and FL93-939. Representative examples of the Venezuelan equine encephalitis virus are TC-83, ZPC738 and 3908. Furthermore, the chimeric DNA may have protein content that is identical to wild-type Chikungunya virus.

The present invention is also directed to a vector comprising DNA described herein, a host cell comprising and expressing the vector and an attenuated chimeric Chikungunya virus comprising the DNA described herein. The present invention is further directed to a pharmaceutical composition comprising the attenuated chimeric Chikungunya virus described supra and a pharmaceutically acceptable carrier.

The present invention is still further directed to an immunogenic composition comprising a live attenuated chimeric Chikungunya virus described herein. The present invention is also directed to a method of protecting an individual for infections resulting from exposure to Chikungunya virus, comprising administering an immunologically effective amount of an immunogenic composition comprising the live attenuated chimeric Chikungunya virus described herein, where the composition elicits an immune response against the Chikungunya virus in the individual, thereby protecting the individual from the infections. Such a method may be beneficial to a human or an animal.

Alternatively, the present invention is directed to an immunogenic composition comprising an inactivated chimeric Chikungunya virus, where the virus comprises the attenuated chimeric Chikungunya virus described herein that is inactivated. The present invention is also directed to a method of protecting an individual for infections resulting from exposure to Chikungunya virus, comprising administering a immunologically effective amount of the immunogenic composition comprising the inactivated chimeric Chikungunya virus described herein, where the composition elicits an immune response against the Chikungunya virus in the individual, thereby protecting the individual from infection. Such a method may be beneficial to a human or an animal. Generally, the infections may arise due to natural exposure or from a bioterror attack.

The present invention is further directed to a method of determining the presence of an antibody to the Chikungunya virus in a subject, comprising: obtaining a serum sample from the subject, and performing an assay using the attenuated chimeric Chikungunya virus described herein to determine the presence or absence of antigenic reactions, effect on physical properties of the Chikungunya virus or a combination thereof in the serum sample, thereby determining the presence of antibody to Chikungunya virus in the subject. Examples of such assays are not limited to but may include enzyme linked immunosorbent assays, hemagglutination inhibition assay, complement fixation assay or plaque reduction neutralization assay. Additionally, the serum may be obtained from a human or an animal.

Alternatively, the present invention is further directed to a method of determining the presence of an antibody to Chikungunya virus in a subject, comprising: obtaining a serum sample from the subject, and performing an assay using an inactivated chimeric Chikungunya virus, where the inactivated chimeric Chikungunya virus comprises the attenuated chimeric Chikungunya virus described herein that is inactivated to determine the presence or absence of antigenic reactions, the effect on physical properties of the Chikungunya virus or a combination thereof in the serum sample, thereby determining the presence of an antibody to Chikungunya virus in the subject. All other aspects regarding the type of assays and the subject is as discussed supra.

The present invention is still further directed to a kit comprising: an attenuated chimeric Chikungunya virus described herein, an attenuated chimeric Chikungunya virus described herein that is inactivated or combinations thereof. Furthermore, the kit may also comprise attenuated and/or inactivated forms of other related chimeric viruses (VEEV, eastern equine encephalitis virus or any related viruses) that are constructed based on the same principles as discussed herein.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof.

The composition described herein can be administered independently, either systemically or locally, by any method standard in the art, for example, subcutaneously, intravenously, parenterally, intraperitoneally, intradermally, intramuscularly, topically, or nasally. Dosage formulations of the composition described herein may comprise conventional non-toxic, physiologically or pharmaceutically acceptable carriers or vehicles suitable for the method of administration and are well known to an individual having ordinary skill in this art.

The composition described herein may be administered independently one or more times to achieve, maintain or improve upon a therapeutic effect. It is well within the skill of an artisan to determine dosage or whether a suitable dosage of the composition comprises a single administered dose or multiple administered doses. An appropriate dosage depends on the subject's health, the induction of immune response and/or prevention of infection caused by Chikungunya virus, the route of administration and the formulation used.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLES

The alphavirus backbones characterized herein include Venezuelan equine encephalitis virus attenuated vaccine strain TC-83 and a South American strain of EEEV, BeAr436087, whose distinguishing feature is its inability to cause disease in adult mice, horses and marmosets despite the induction of viremia. The rationale for using EEEV and Venezuelan equine encephalitis virus TC-83 backbones is strongly supported by identification of Venezuelan equine encephalitis virus- and EEEV-specific capsids as strong molecular determinants of viral pathogenesis. EEE/SINV and VEE/SINV chimeric viruses (that are very similar to the proposed chimeras with CHIKV-specific structural genes) which lack the VEEV and EEEV pathogenic capsid genes, were nonpathogenic for mice, incapable of causing profound cytopathic effects in tissue culture and did not interfere with the development of innate immune responses.

Figure 1:
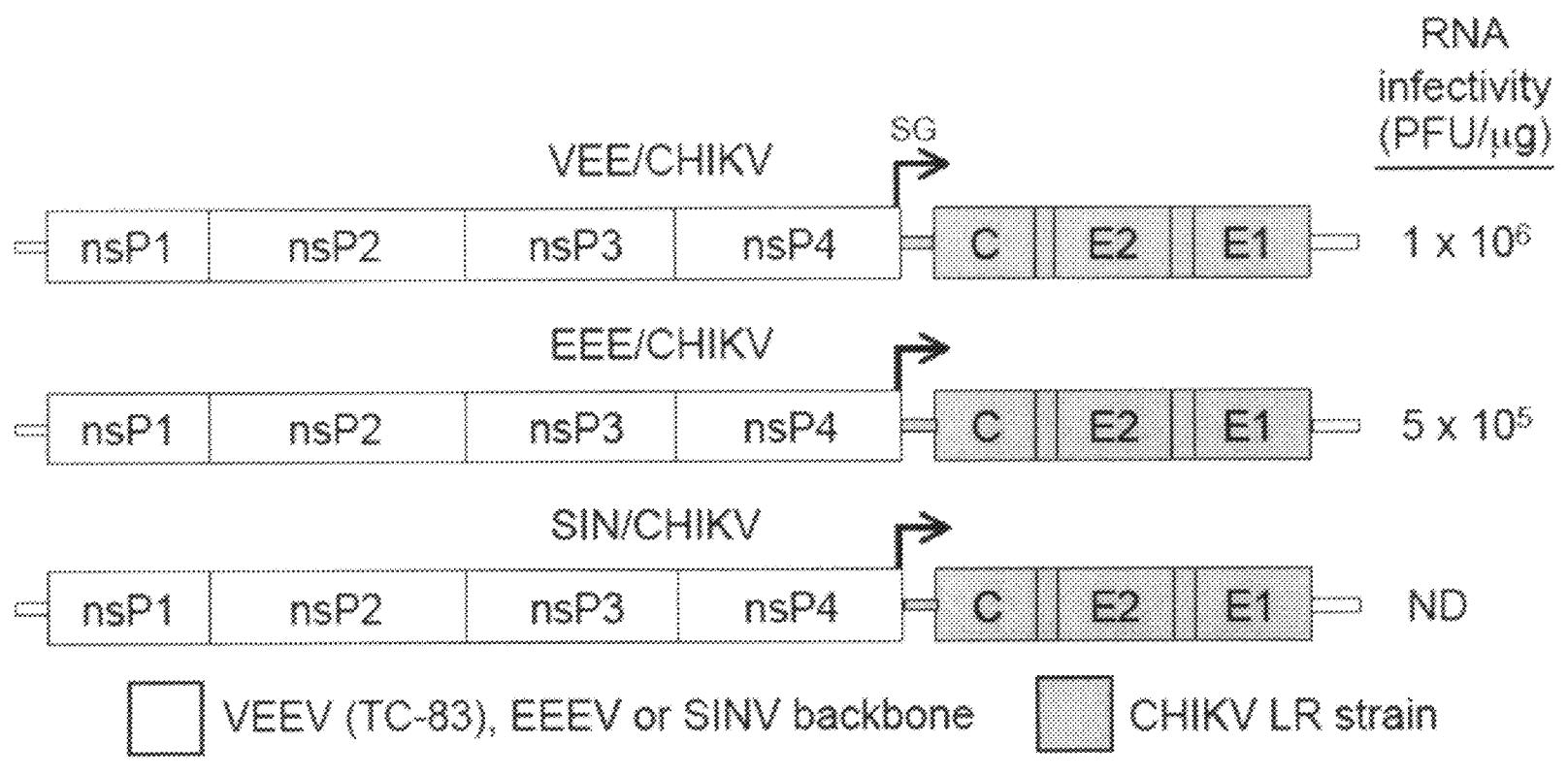

To design the recombinant cDNAs for chimeric Chikungunya virus, the Venezuelan equine encephalitis virus-, and EEEV-specific structural polyprotein-coding sequence was replaced by the corresponding Chikungunya virus genes (FIG. 1). The nsPs and cis-acting RNA elements (that include 5' and 3' termini and subgenomic promoters) remained backbone-specific. Both of the designed recombinants, VEE/CHIKV and EEE/CHIKV were viable and capable of replication in cell culture, with titers in Vero cells approaching $10^9$ infectious units/ml.

Evaluation of Chimeric CHIKV Vaccine Candidates in Mice

Figure 2:
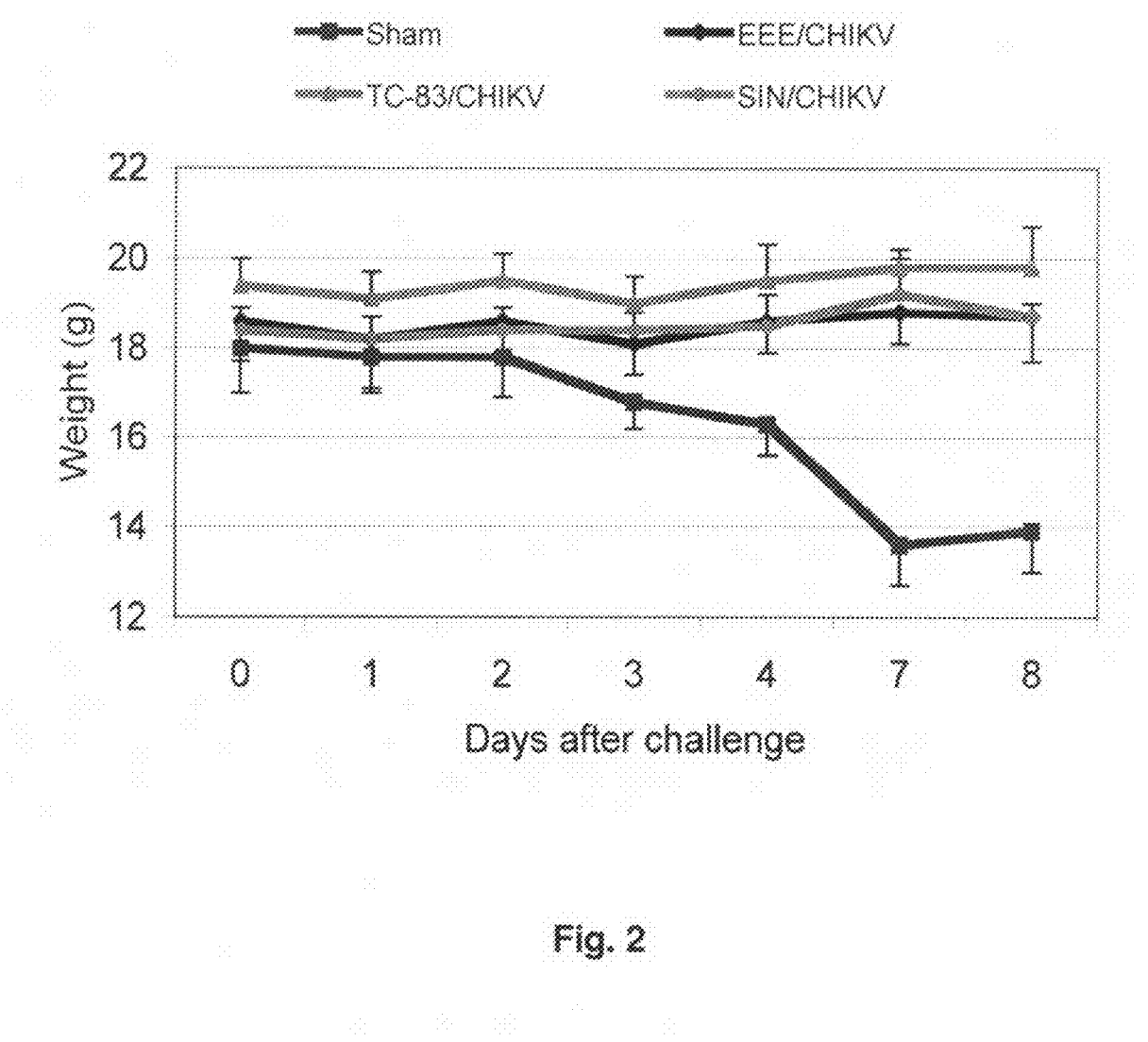

Virus that were generated from the 3 clones by electroporation of Vero cells were passaged once in Vero cells and used to vaccinate small cohorts of 5 week old C57BL/6 mice SC. After 3 weeks, the mice were bled and evaluated by PRNT. No viremia, alterations in weight gain or signs of disease were noted compared to sham-vaccinated controls. As shown in Table 1, all mice seroconverted with mean antibody titers of 53-80, and all vaccines prevented detectable viremia (sham-vaccinated mice had mean titers of 2.5 and 2.0 $\text{Log}_{10}$ PFU/ml on days 1 and 2, respectfully) disease and weight loss after challenge with the Ross strain (FIG. 2). The EEE/CHIK and TC-83/CHIK chimeras were further evaluated by vaccinating cohorts of ten 3 week old NIH Swiss mice. All of the mice seroconverted with mean titers of 116-136 (Table 2); no viremia (sham-vaccinated mice had mean titers of 3.3 and 3.2 $\text{Log}_{10}$ PFU/ml on days 1 and 2, respectively), alterations in weight gain or signs of disease were detected. Both vaccines prevented weight loss observed in the sham vaccinated animals (not shown). SIN/CHIKV chimera was less efficient in replication in tissue culture, induced less efficient immune response in mice and does not represent a promising vaccine candidate. These data indicate that the chimeric vaccine candidates were attenuated and immunogenic in mice and prevent viremia and disease.

TABLE 1

PRNT antibody titers in C57BL/6 mice 3 weeks after infection with chimeric CHIKV vaccine candidates.

| Virus strain | Dose | Number seropositive* | Mean antibody titer ± SD |
|---|---|---|---|
| EEE/CHIKV | 5.8 | 5/5 | 80 ± 49.0 |
| TC-83/CHIKV | 5.6 | 5/5 | 72 ± 17.9 |
| SIN/CHIKV | 6.2 | 3/3 | 53 ± 23.1 |

*80% plaque reduction neutralization titer ≧ 20.

TABLE 2

PRNT antibody titers in NIH Swiss mice 3 weeks after infection with chimeric CHIKV vaccine candidates.

| Virus strain | Dose | Number seropositive* | Mean antibody titer ± SD |
|---|---|---|---|
| EEE/CHIKV | 5.3 | 10/10 | 116 ± 89 |
| TC-83/CHIKV | 5.8 | 10/10 | 136 ± 83 |

*80% plaque reduction neutralization titer ≧ 20.

Cells

Baby hamster kidney (BHK-21) and Vero African green monkey kidney cells were purchased from the American Type Culture Collection (Bethesda, Md.) and grown at 37° C. in Eagles minimal essential medium (MEM) with 10% fetal bovine serum (FBS) and 0.05 mg/ml of gentamycin sulfate (Invitrogen, Carlsbad, Calif.). The *Aedes albopictus* mosquito cell line C7/10 (from H. Huang, Washington Univ.) was maintained in MEM at 32° C. with 10% FBS and 10% tryptose phosphate broth.

Viruses

Chikungunya virus strains La Réunion (LR) and Ross were used for cDNA production and challenge experiments. Strain LR, isolated from a human during the 2006 La Réunion outbreak, was passaged five times in Vero cell culture and once in infant mice before RNA extraction and cDNA cloning. Virus was rescued from this infectious clone by electroporating viral RNA into C7/10 cells as described previously [Tsetsarkin et al, Vector Borne Zoonotic Dis 2006 Winter; 6(4):325-37.]. The Ross strain, isolated from a human during the 1953 Tanzania epidemic, was passaged 175 times in newborn mice, twice in Vero cells, and once in C7/10 cells.

Construction of Recombinant Alphavirus/CHIKV Plasmids

Chimeric alphavirus/CHIKV vaccine viruses were created using recombinant DNA methods as described [Wang et al. Vaccine 2007 Oct. 23; 25(43):7573-81]. The alphavirus backbones used included Sindbis virus (SINV) strain AR339, the attenuated VEEV vaccine strain TC-83, and a South American strain of EEEV, BeAr436087, whose distinguishing feature is the inability to cause disease in adult mice or marmosets despite the induction of viremia. To design the recombinant cDNAs, the VEEV-, EEEV- and SINV-specific structural polyprotein-coding sequences were replaced with the corresponding CHIKV LR strain genes. The nsPs and cis-acting RNA elements (that include 5' and 3' termini and subgenomic promoters) remained backbone-specific.

In Vitro Transcription, Transfection and Production of Chimeric Viruses

Plasmids were purified by centrifugation in CsCl gradients. Before the transcription reaction, the viral and replicon genome-coding plasmids were linearized by XhoI digestion. RNAs were synthesized by SP6 RNA polymerase in the presence of cap analog. The yield and integrity of transcripts were analyzed by gel electrophoresis under non-denaturing conditions. Aliquots of transcription reactions were used for electroporation without additional purification.

Electroporation of BHK-21 cells was performed under described conditions [Paessler et al., J Virol 2003 September; 77(17):9278-86]. To rescue the viruses, 1 mg of in vitro-synthesized viral genome RNA was electroporated into cells, which were then seeded into 100-mm dishes and incubated until cytopathic effects (CPE) were observed. Virus titers were determined using a standard plaque assay on BHK-21 cells. To assess the RNA infectivity, 10-fold dilutions of electroporated BHK-21 cells were seeded in 6-well plates. After 1 h incubation at 37° C. in a 5% $CO_2$ incubator, cells were overlaid with 2 ml 0.5% agarose supplemented with MEM and 3% FBS. Plaques were stained with crystal violet after 2 days incubation at 37° C., and infectivity was determined as PFU per mg of transfected RNA. Passaging of recombinant viruses in Vero cells was performed by infecting cells in 35-mm dishes with 10 ml of viral stocks, harvested on the previous passage. Viruses were harvested after developing profound CPE and titers were determined by plaque assay on BHK-21 and/or Vero cells.

Analysis of Viral Structural Protein Synthesis

BHK-21 cells were seeded into 6-well plates and infected with different viruses at a multiplicity of infection (MOI) of 20 PFU/cell. At 16 h post infection, the cells were incubated for 30 min in 0.8 ml of DMEM medium lacking methionine and supplemented with 0.1% FBS and 20 mCi/ml of [$^{35}$S] methionine. After this incubation, they were scraped into the media, collected by pelleting at 1500 rpm, and dissolved in 100 ml of standard protein loading buffer. Equal amounts of proteins were loaded onto each lane of the sodium dodecyl sulfate (SDS)-10% polyacrylamide gels. After electrophoresis, the gels were dried, autoradiographed and analyzed on a Storm 860 PhosphorImager (Molecular Dynamics, Sunnyvale, Calif.).

Mouse Infections

NIH Swiss and C57BL/6 mice were purchased from Harlan Sprague Dawley, Inc. (Indianapolis, Ind.) and maintained under specific-pathogen-free conditions. To monitor body temperature, 3-week-old or older mice were anaesthetized with isofluorane 3 days before infection and implanted subcutaneously (SC) with a pre-programmed telemetry chip according the manufacturer's instructions (IPTT-300; Bio Medical Data Systems, Inc., Seaford, Del.). Body temperatures and weights were recorded daily/weekly without anesthesia. Three-week or older mice were infected with CHIKV SC in the medial thigh or intraperitoneally (IP) in a total volume of 100 µl. Intranasal infections (IN) used a dose of 6.5 $log_{10}$ PFU in a total volume of 25 µl. Blood samples were collected from the retroorbital sinus and virus titers were determined by plaque assay on Vero cells [37]. Infant mice were infected intracerebrally (IC) or SC in the dorsal shoulder region in a volume of 20 or 50 µl, respectively.

Immunizations and Challenges with CHIKV

Three week-old mice were vaccinated SC in the medial thigh. Controls were sham-infected with phosphate buffered saline (PBS). Blood samples were collected from the retroorbital sinus to detect viremia for 3 days after vaccination. Animals were checked daily to observe clinical signs of infection, and body weights were monitored on days 1-7, 14 and 21 after vaccination. Sera were collected on day 21 after vaccination and a plaque reduction neutralization test (PRNT) was performed to examine antibody (Ab) responses. Mice were then challenged with the Ross CHIKV strain at a dose of 6.5 $\log_{10}$ PFU by the IN route.

Histopathology and Immunohistochemical Staining

On days 3 and 7 post-infection, 3 animals per group of 5-week-old female C57BU6 mice (14-16 g) infected with the Ross CHIKV strain and age-matched, sham infected mice were bled and sacrificed, and tissues (brain, heart, lung, liver, spleen, kidney, and skeletal muscle) were collected and titered for virus. Brain tissues were also fixed in 10% buffered formalin solution for 24 h, then stored in 70% ethanol prior to embedding, sectioning, and staining using hematoxylin and eosin (H&E) and immunohistochemistry. For immunohistochemistry, the formalin-fixed, paraffin-embedded tissue sections (3-4 μm thick) were deparaffinized and immersed in 3% $H_2O_2$ for 30 min to block endogenous peroxidase activity. This was followed by an antigen retrieval step with 10% target retrieval solution (DAKO, Carpinteria, Calif.) at 90° C. for 30 min. CHIKV mouse hyperimmune ascitic fluid was used as the primary Ab at a dilution of 1:150, and bound primary Ab was directly labeled and detected by use of a commercially available mouse-on-mouse Iso-IHC AEC kit (InnoGenex, San Ramon, Calif.). Primary Ab against a flavivirus, Modoc virus (MODV), was used as a negative control.

Design of Chimeric Viruses

Chimeric viruses, with the replicative enzymes of one alphavirus in combination with the structural proteins derived from another, demonstrate highly attenuated phenotypes in vivo using small animal models. However, these chimeric alphaviruses elicited efficient immune responses against the viruses whose structural genes were used in the chimeric design. The present invention developed new vaccine candidates against CHIKV by producing 3 different recombinant alphaviruses expressing CHIKV structural protein genes. The nonstructural protein genes, both 5'-and 3'-specific cis-acting promoter elements, and the subgenomic promoters in the recombinant genomes were derived either from VEEV vaccine strain TC-83, EEEV strain BeAr436087, or SINV strain AR339; the structural genes and 5'UTR of the subgenomic RNA were derived from the LR strain of CHIKV. This design was aimed at promoting i) the most efficient replication of viral genomes, ii) transcription of the subgenomic RNA (which were achieved by using nonstructural protein gene promoter elements from the same virus), and iii) efficient translation of the structural protein genes by using the 5'UTR from the same virus as the structural protein genes. Nonstructural protein 2 (nsP2) appears to serve this function. Therefore, combination of VEEV and EEEV nsPs and CHIKV structural protein genes (including the capsid) in chimeric genomes results in attenuation. The rationale for the SIN/CHIKV chimera design was also based on inefficient replication of SINV in vivo in mammals. Thus, the use of SINV-specific replicative enzymes in combination with heterologous, CHIKV-specific structural proteins generates a virus with attenuated phenotype that results from its inefficient replication in vivo.

All of the recombinant viral genomes were synthesized in vitro by using SP6 DNA-dependent RNA polymerase and transfected into BHK-21 cells by electroporation. Fractions of electroporated cells were used for an infectious center assay and the rest of the cells were used to generate viral stocks. The VEE/CHIKV and EEE/CHIKV constructs demonstrated high specific infectivities in the infectious center assay, ca. $1\times10^6$ and $5\times10^5$ PFU/mg of RNA, respectively, indicating that these viruses were capable of replication and causing CPE without accumulating additional, adaptive mutations in their genomes. In contrast, the SIN/CHIKV chimera did not form detectable plaques in the infectious center assay, but ultimately caused CPE under liquid medium. This indicated that the original SIN/CHIKV chimeric genome was capable of replication, but did not develop productive, spreading infection to produce plaques; most likely, accumulation of additional adaptive mutations was required for more efficient virus replication.

Adaptation of the Chimeric Viruses to Replication in Cell Culture

The CHIKV structural protein genes were originally derived from a virus isolate that was passaged only 5 times in cell culture. However, alphaviruses are notorious for their ability to accumulate the adaptive mutations in the envelope proteins that increase their positive charge for enhanced binding to heparan sulphate, leading to more efficient replication. Therefore, the adaptation was analyzed of not only of the SIN/CHIKV chimera, but of all of the recombinants, to replication in Vero cells, which are approved vaccine substrates. The SIN/CHIKV (original, very low titer stock), VEE/CHIKV and EEE/CHIKV chimeric viruses were passaged 3 times in Vero cells as described above, and titers of stocks, harvested after the third passage at 24 and 48 h post infection, are presented in Table 3.

TABLE 3

Titers of chimeric alphaviruses found in Vero cell passage 3 supernatants after infection at a multiplicity of approximately 1.

| | Cells used for plaque assay | | | |
| --- | --- | --- | --- | --- |
| | Vero | | BHK-21 | |
| Virus | 24 h | 48 h | 24 h | 48 h |
| VEE/CHIKV | $2 \times 10^8$ | $1.5 \times 10^8$ | $1.5 \times 10^8$ | $1.25 \times 10^8$ |
| EEE/CHIKV | $5 \times 10^7$ | $4 \times 10^7$ | $7.5 \times 10^7$ | $1 \times 10^8$ |
| SIN/CHIKV | $5 \times 10^7$ | $5 \times 10^7$ | $7 \times 10^6$ | $7 \times 10^6$ |

All of the chimeras continued to develop heterogeneous plaque sizes even after 3 passages, indicating the presence of different genetic variants in the viral populations. Therefore, to generate more homogeneous and genetically stable vaccine stocks for testing, 2 plaques were randomly selected for each chimera and used to generate new stocks and to sequence their viral genomes; large plaques were preferentially selected to maximize yields.

Titers of virus stocks, prepared from Vero cells 24 h after infection with individual plaque clones, are presented in Table 4. The plaque-purified variant of VEE/CHIKV with the higher titer (plaque 1) had two mutations, N72→Y and S159→R, in the E2 glycoprotein, and the variant with the lower titer had no mutations in the structural genes. Both isolates of EEE/CHIKV had the same W64R mutation in the E2 glycoprotein, and the SIN/CHIKV isolates had mutation E2 substitution E150→K and a deletion of nt 9, located in the 5'UTR of the subgenomic RNA. This and all other E2 mutations found in the recombinant viruses increased the positive charge of this glycoprotein and most likely adapted them for more efficient binding to and replication in Vero cells. Such variants are therefore probably more suitable for large-scale vaccine production.

TABLE 4

Titers in Vero cell cultures 24 hours after infection with plaque-purified chimeric alphaviruses.

|  | VEE/CHIKV | EEE/CHIKV | SIN/CHIKV |
|---|---|---|---|
| Plaque 1 | $2.5 \times 10^9$ | $1.15 \times 10^9$ | $1 \times 10^8$ |
| Plaque 2 | $2 \times 10^7$ | $1.1 \times 10^9$ | $1.5 \times 10^8$ |

The nt 9 mutation was interesting because it could explain the ability of this variant to spread more efficiently. Therefore, the modified 5'UTR was transferred into the original SIN/CHIKV genome, and the in vitro-synthesized RNA of this variant, SIN/CHIKVD9, indeed demonstrated in the infectious center assay an infectivity of $2-5 \times 10^6$ PFU/mg of RNA that was comparable to infectivities of other recombinant genomes. This was an indication that this mutation had a dramatically positive effect on the ability of virus to productively replicate in cell culture.

Recombinants produced similar levels of CHIKV structural proteins. BHK-21 cells were infected with VEE/CHIKV, EEE/CHIKV and SIN/CHIKVD9 at the same MOI, and at 16 h post infection, cells were metabolically labeled with [$^{35}$S]methionine. Cell lysates were analyzed by electrophoresis in SDS-10% polyacrylamide gels. All of the viruses produced similar levels of the virus-specific structural proteins (FIG. 3), indicating that all of them were suitable for further development as candidate vaccines.

Mouse Models for CHIKV

Because little research has been done on animal models for CHIKV, a murine challenge model was developed. Initially, cohorts of three 10-week-old (to allow for vaccination at an age of 6 weeks and challenge at 10 weeks) NIH Swiss mice were infected with the LR and Ross strains by the SC, IP and IN routes. The LR isolate was used because it represents CHIKV strains circulating recently in the Indian Ocean and India, and the Ross strain was selected because of its extensive mouse passage history, which may have increased virulence. Animal body temperatures and weights were monitored daily, and blood was collected daily up to 4 days postinfection. Viremia was detected on day 1 after IN infection in all 3 animals infected with the LR strain (mean titer $\log_{10}$ 2.8 PFU/ml±0.2), but none was detected thereafter. No viremia was detected in the Ross group 24 hr after IN infection, and one mouse developed viremia on day 2 after IN infection ($\log_{10}$ 3.2 PFU/ml). No detectable viremia occurred on days 3-4 after infection in any of the cohorts. No febrile response was detected, nor weight loss or other signs of disease.

In an attempt to produce more disease for comparative attenuation evaluations, cohorts of 5-week-old (rather than 10-week-old) inbred C57BU6 or outbred NIH Swiss mice were infected using the IP and IN routes. As shown in Table 5, both CHIKV strains delivered IN produced viremia lasting 2-3 days with a peak titer of about 3 $\log_{10}$ PFU/ml, while IP infection yielded less consistent results. Only the Ross strain produced clinical signs of disease after IN infection; all animals exhibited ruffled fur, a hunched posture, and inactivity by day 6 and died by day 7 or 8 after infection. NIH Swiss mice had similar viremia titers after IN infection, but no signs of infection. All other groups remained apparently healthy.

TABLE 5

Viremia in 5 week-old, female C57BL/6 mice infected with CHIKV

| Virus strain | Number tested | Route of inoculation* | Mean viremia 24 h after infection ($\log_{10}$ PFU/ml ± SD) | Mean viremia 48 h after infection ($\log_{10}$ PFU/ml ± SD) | Mean viremia 72 h after infection ($\log_{10}$ PFU/ml ± SD) |
|---|---|---|---|---|---|
| LR | 3 | IN | <0.9 | 2.6 ± 0.7 | 2.4 ± 0.3 |
|  | 3 | IP | 3** | <0.9 | 2.3** |
| Ross | 3 | IN | 2.6 ± 0.5 | 2.5 ± 0.3 | <0.9 |
|  | 4 | IP | 2.3 ± 0.4*** | <0.9 | <0.9 |

*IN, intranasal; IP, intraperitoneal; Doses: 7.8 $\log_{10}$ PFU (IP) or 6.5 $\log_{10}$ PFU (IN);
**One mouse was positive;
***Two mice were positive To assess pathologic changes, a separate experiment was conducted in which, in addition to viremia measurements, 3 C57BU6 mice were euthanized 3 or 7 days after IN infection with the Ross CHIKV strain. Virus titers in the brain were high on both days 3 and 7 post infection, with the highest titers over 7 $\log_{10}$ PFU/g. On day 3, all animals also had detectable virus in the heart, and one mouse had infectious virus in the kidney and skeletal muscle of the leg (Table 6). No viremia was detected after day 2 after infection, and on day 7 after infection, no virus was detected in any organ except for the brain.

TABLE 6

Ross strain CHIKV titers in 5-week-old C57BL/6 mice after intranasal infection

| Organ/tissue | Virus titer ($\log_{10}$ PFU/ml or g ± SD) | |
|---|---|---|
|  | Day 3 | Day 7 |
| Blood | <0.9 | <0.9 |
| Brain | 7.1 ± 0.5 | 6.2 ± 1.3 |
| Heart | 2.9 ± 0.7 | <0.9 |
| Lung | 2.9 ± 0.9** | <0.9 |
| Liver | <0.9 | <0.9 |
| Spleen | 2.2* | <0.9 |
| Kidney | <0.9 | <0.9 |
| Muscle | 2.1* | <0.9 |

*One mouse was positive;
**Two mice were positive

Signs of disease in the 5-week-old C57BL/6 mice infected with the Ross strain included a reduction in body weight gain beginning by day 5 post-infection (p<0.05, ANOVA with Tukey-Kramer multiple comparisons test) and continuing until death (p<0.001). No significant febrile response was detected; however, some mice had slight elevations in body temperature (38-38.5° C.) on 1 or 2 days after infection.

Histopatholoqic Evaluation and Immunohistochemical Detection of CHIKV Antigen:

Upon histopathological analysis, the CHIKV (Ross strain)-infected brains of the 5-week-old C57BU6 mice on day 3 after infection showed minimal perivascular mononuclear cellular infiltration that was located in focal areas of the cerebral cortex. Throughout the deep cerebral cortex, there were mild increases in the number of microglial cells as well as diffuse areas of neuronal degeneration and apoptosis. Nuclear fragmentation of neurons, expressed as nuclear dust, was also found in focal areas of the deep cerebral cortex, and in the cerebellum, some Purkinje neuron cells showed condensation and degeneration.

On day 7 after infection, the CHIKV-infected brains showed severe, multifocal inflammation and liquefactive necrosis in the cerebral cortex (FIG. 4). In regions of the superficial cerebral cortex, severe spongiform changes and a large number of apoptotic bodies and microglial cells were evident. Composed primarily of lymphocytic cells, perivascular cuffs were located diffusely throughout the cerebral cortex. Similar to the lesions in the cerebral cortex, focal areas of severe spongiform changes, liquefactive necrosis, and neuronal degeneration were found in the hippocampus, and there was multifocal lymphocytic leptomeningitis.

Based on immunohistochemical staining, CHIKV antigen was detected in the brain of the C57BU6 mice on days 3 and 7 after IN infection. On day 3 post-infection, clusters or individual neurons with antigen-positive cytoplasmic staining were observed in multifocal areas of the cerebral cortex. Other regions of the brain were negative. By day 7 after infection, the number of positive staining neurons had increased that were primarily located in the necrotic areas of the cerebral cortex (FIG. 4) and hippocampus.

Based on these murine model results, the vaccine attenuation studies focused on SC infection of 3-week-old mice as well as 2 more sensitive models of disease developed previously: IC infection of 6-day-old mice as a measure of neurovirulence, as well as SC infection of 3-4-day-old mice as a measure of viremia induction, peripheral replication in muscle and joint tissue, and neuroinvasion.

Attenuation and Immunogenicity of Vaccine Candidates

Figure 5:
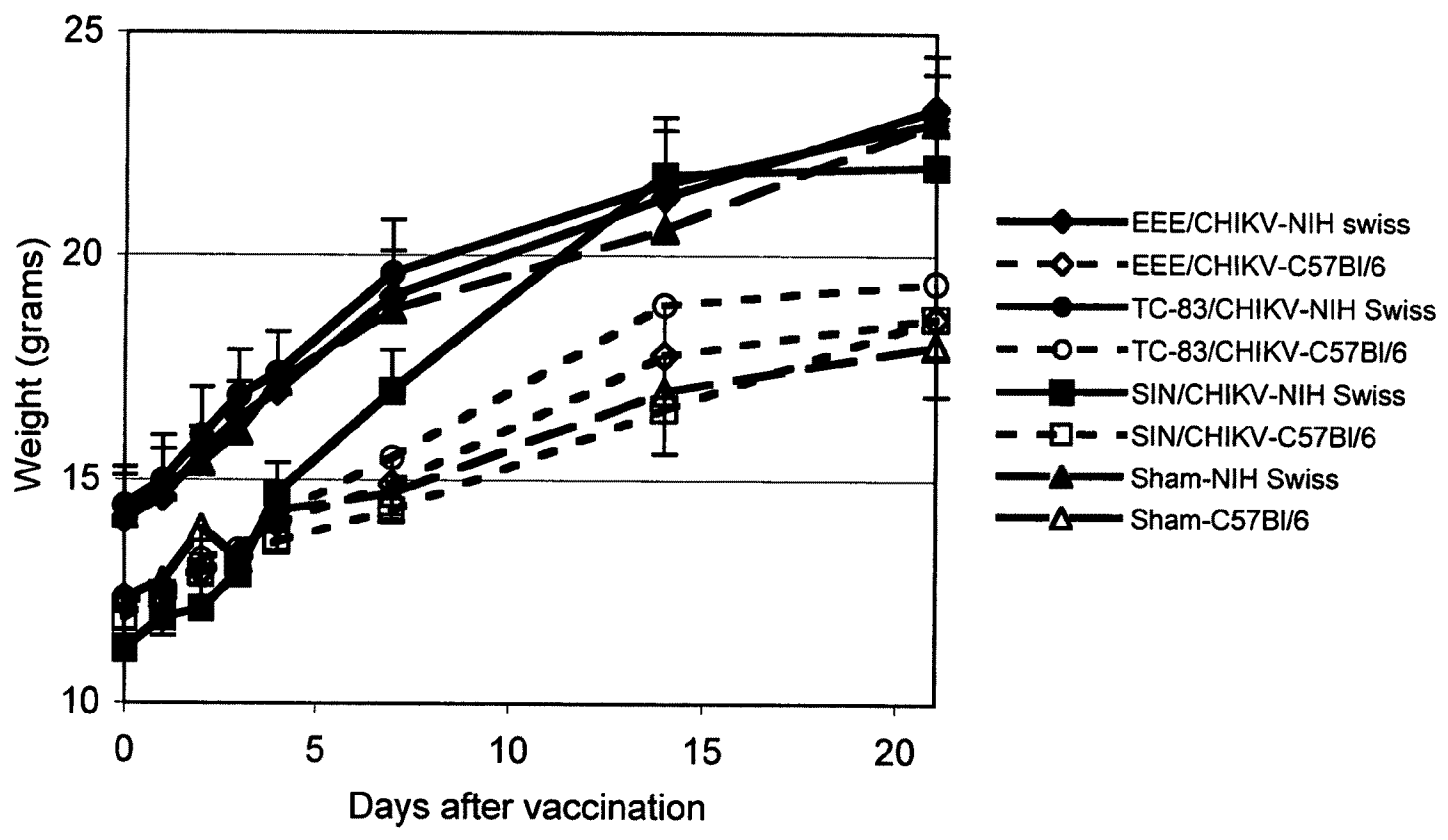

To assess attenuation of the chimeric CHIKV vaccines, 3 week-old female C57BU6 mice (5 per cohort) and NIH Swiss mice (10 per cohort) were inoculated SC with the TC-83/CHIKV, EEE/CHIKV and SIN/CHIKV chimeras at doses of 5.8, 5.3 and 5.8 $\log_{10}$ PFU respectively. No infectious virus was detected in the serum of any vaccinated mice by plaque assay 1-3 days after infection (limit of detection=8 PFU/ml). None of the vaccinated animals exhibited any signs of infection, and continued to gain weight after vaccination (FIG. 5). Three weeks after immunization, sera were collected and Ab responses were assessed by PRNT. All animals had positive ($\geq 20$) titers ranging from 20-320 when tested against the CHIKV LR strain (Table 7).

TABLE 7

Neutralizing antibody titers in mice 3 weeks after immunization with vaccine candidates

| Virus strain | Mouse strain | Vaccine dose ($\log_{10}$PFU) | Number seropositive* | Mean antibody titer ± SD |
|---|---|---|---|---|
| EEE/CHIKV | NIH Swiss | 5.3 | 10/10 | 116 ± 88.8 |
| | C57BL/6 | 5.8 | 5/5 | 80 ± 49.0 |
| TC-83/CHIKV | NIH Swiss | 5.8 | 10/10 | 136 ± 82.6 |
| | C57BL/6 | 5.6 | 5/5 | 72 ± 17.9 |

TABLE 7-continued

Neutralizing antibody titers in mice 3 weeks after immunization with vaccine candidates

| Virus strain | Mouse strain | Vaccine dose ($\log_{10}$PFU) | Number seropositive* | Mean antibody titer ± SD |
|---|---|---|---|---|
| SIN/CHIKV | NIH Swiss | 5.8 | 10/10 | 43 ± 19.7 |
| | C57BL/6 | 5.8 | 5/5 | 40 ± 24.5 |

*80% plaque reduction neutralization titer $\geq 20$

Figure 6:
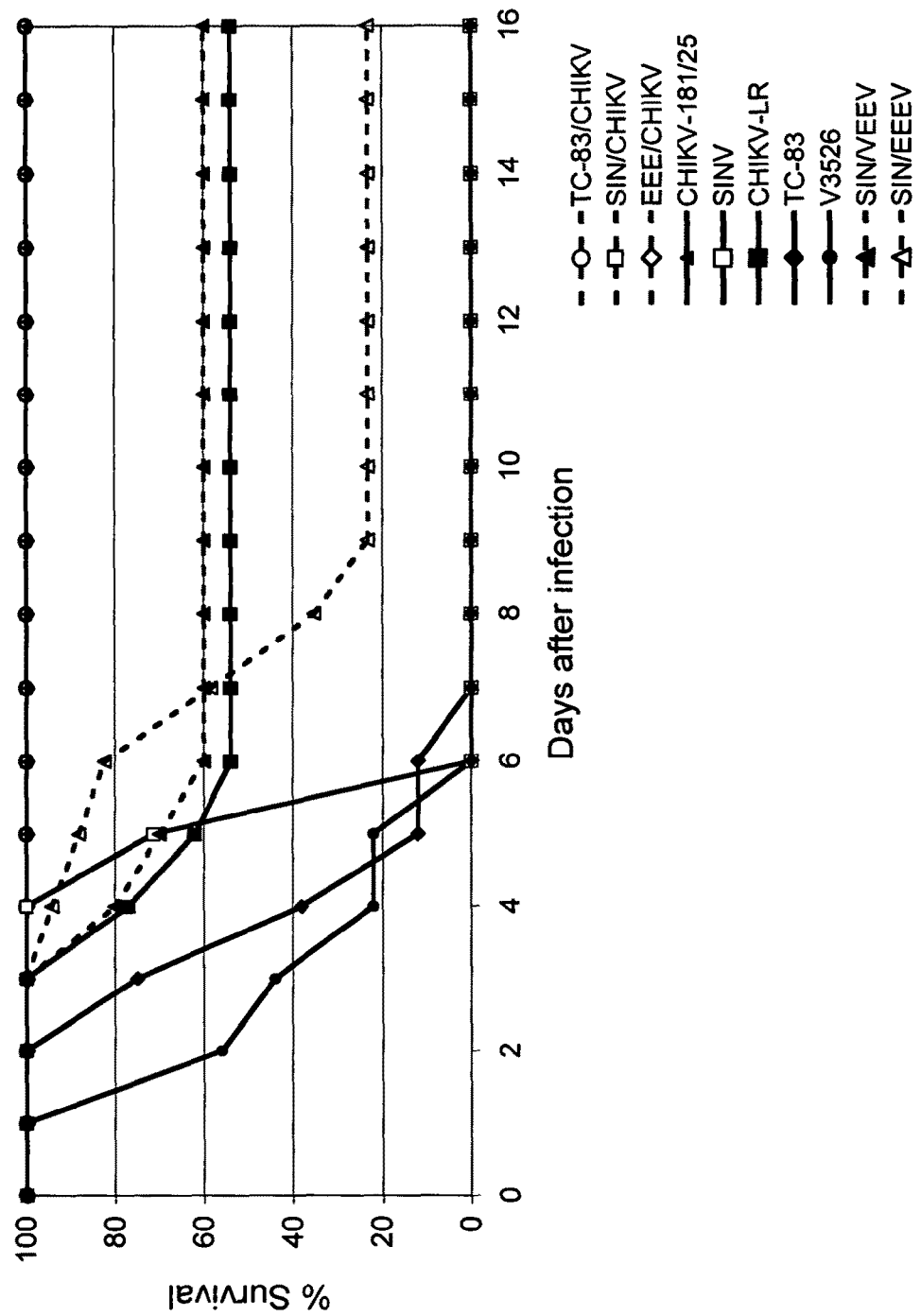
FIG. 6 shows mortality in 6-day-old NIH Swiss mice after IC infection with ca. $10^6$ PFU of chimeric CHIKV vaccine candidates, vaccine strain 181/25, or the wt CHIKV LR strain. Other alphavirus vaccine strains including VEEV strains TC-83, V3526, and chimeric SIN/VEEV and SIN/EEEV are included for comparison.

The chimeric vaccine candidates were also evaluated using the more sensitive newborn mouse IC and SC infection models. IC infection of 6-day-old mice yielded no mortality, while the wild-type (wt) CHIKV LR strain killed approximately half of mice by day 6 (FIG. 6). The survival curves for the chimeras were significantly different from that of the wt LR strain (Logrank test, p=0.001). Other alphavirus vaccines including VEEV strains TC-83, V3526, SIN/VEEV and SIN/EEEV chimeras yielded higher mortality rates than the CHIKV chimeras.

Figure 7A:
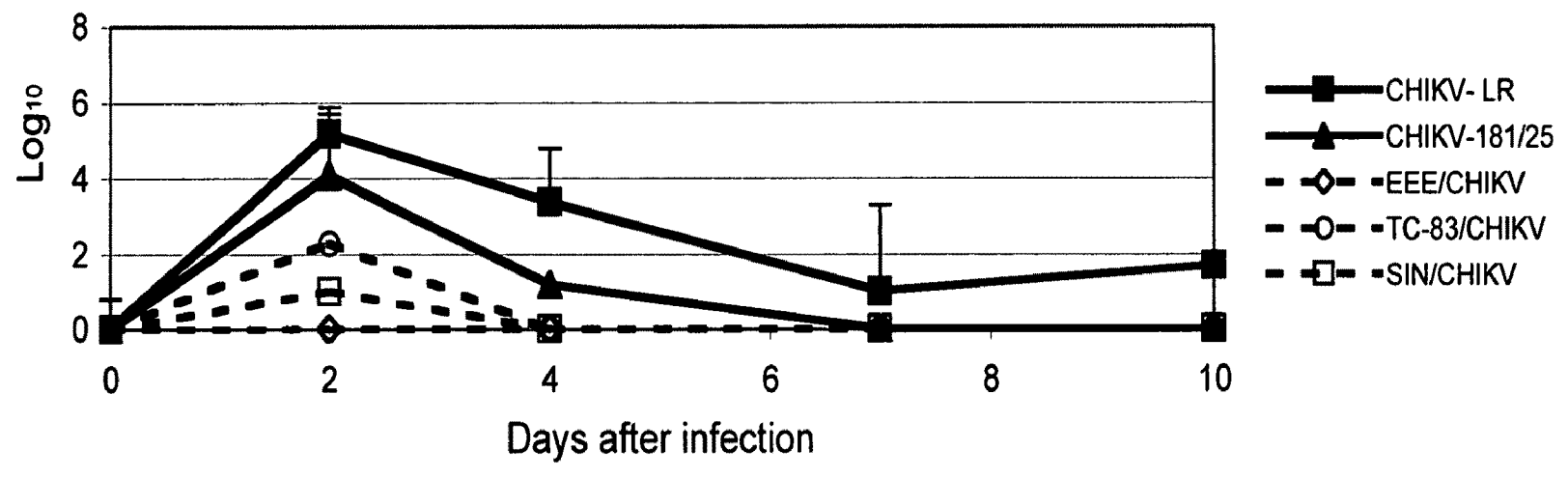
Figure 7B:
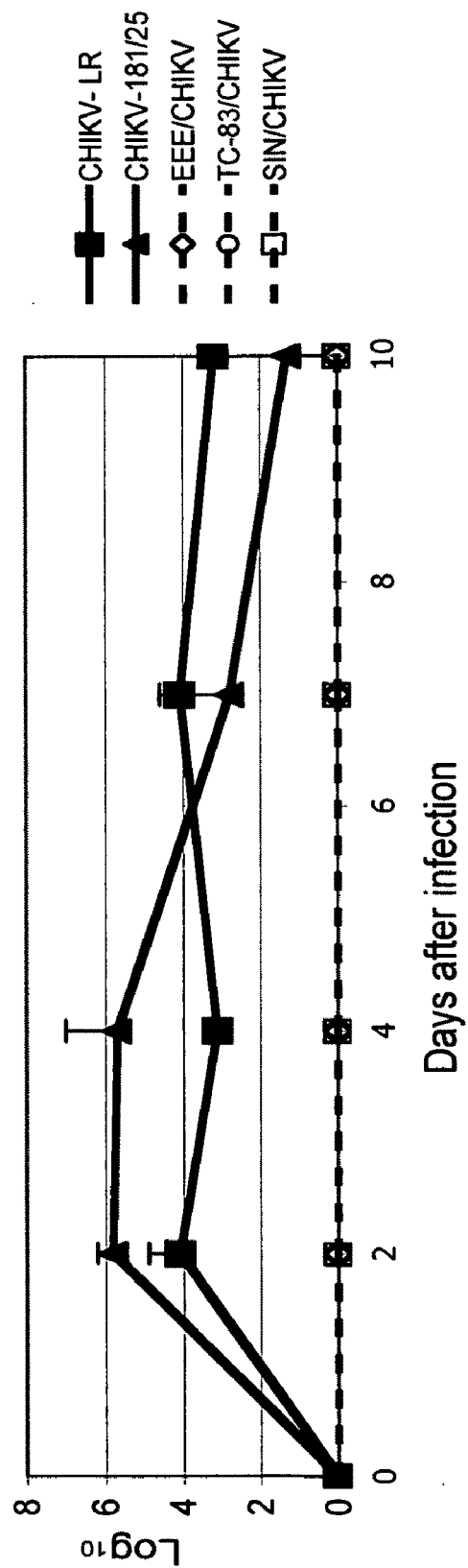
Figure 7C:
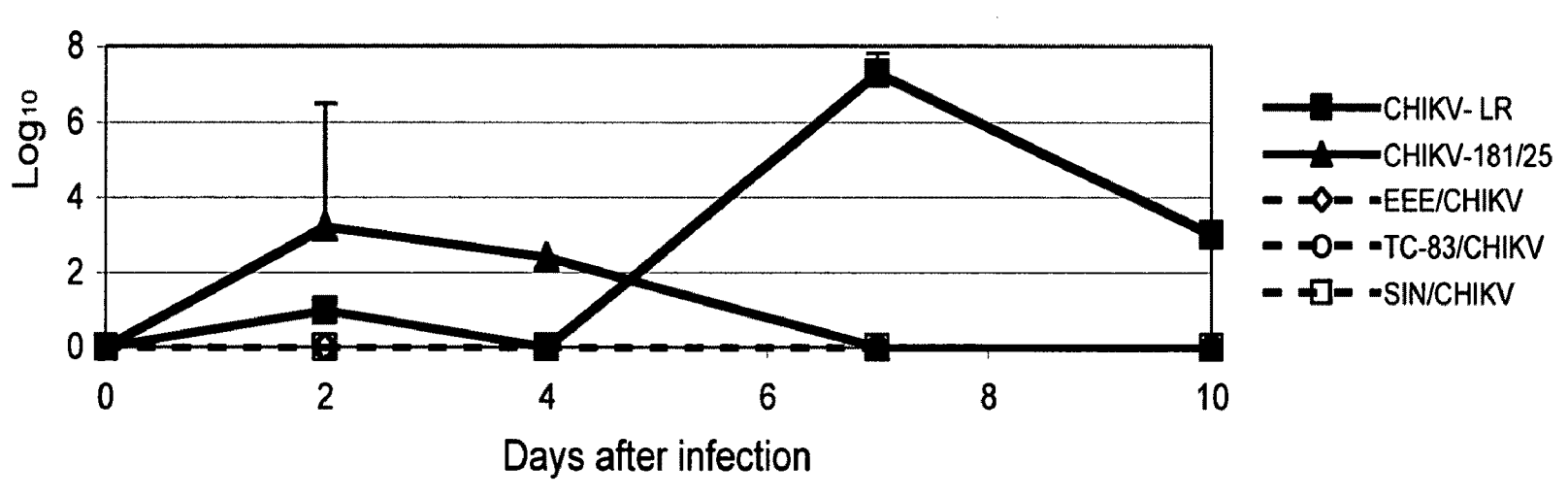

Evaluation of virulence using the 3-4-day SC murine model also yielded evidence of attenuation of the CHIKV chimeras. All produced lower titers and shorter duration of viremia than the wt LR CHIKV or the 181/25 vaccine strain, and there was no evidence of chimera replication in the femorotibial (knee) joints or in the brains 2-10 days after infection (FIGS. 7A-7C).

To assess the immune responses to different vaccine doses, the TC-83/CHIKV and EEE/CHIKV candidates, which appeared to be the most immunogenic (Table 8), were inoculated SC into 3-week-old C57BL/6 mice at doses from 3.8-5.9 $\log_{10}$ PFU. Controls consisted of strain 181/25 (positive) at a dose of 5.5 $\log_{10}$ PFU, and diluent (negative). Mice vaccinated with the chimeric strains all seroconverted, with the highest Ab titers occurring after the highest vaccine doses. However, even the lower chimeric virus doses produced robust mean neutralizing Ab titers >100, and all mice were protected from IN challenge with the neurovirulent Ross CHIKV strain. Survival rates in vaccinated mice were significantly higher than in sham-vaccinated mice (Fisher's exact test, p=0.008). The 181/25 vaccine strain also yielded seroconversion and protection in all mice, but mean Ab titers were lower than those produced by the chimeras at most doses.

TABLE 8

Dose-response in neutralizing antibodies and protection from challenge* 3 weeks after vaccination of C57BL/6 mice

| Vaccine strain | Vaccine dose ($\log_{10}$PFU) | Number seropositive** | Mean antibody titer ± SD | Survival after challenge |
|---|---|---|---|---|
| EEE/CHIKV | 5.9 | 5/5 | 200 ± 80 | 5/5 |
| | 4.9 | 5/5 | 144 ± 36 | 5/5 |
| | 3.9 | 5/5 | 112 ± 44 | 5/5 |
| TC-83/CHIKV | 5.8 | 5/5 | 260 ± 120 | 5/5 |
| | 4.8 | 5/5 | 256 ± 88 | 5/5 |
| | 3.8 | 5/5 | 224 ± 88 | 5/5 |
| 181/25 | 5.5 | 5/5 | 144 ± 115 | 5/5 |
| Sham | | 0/5 | | 0/5 |

Figure 8:
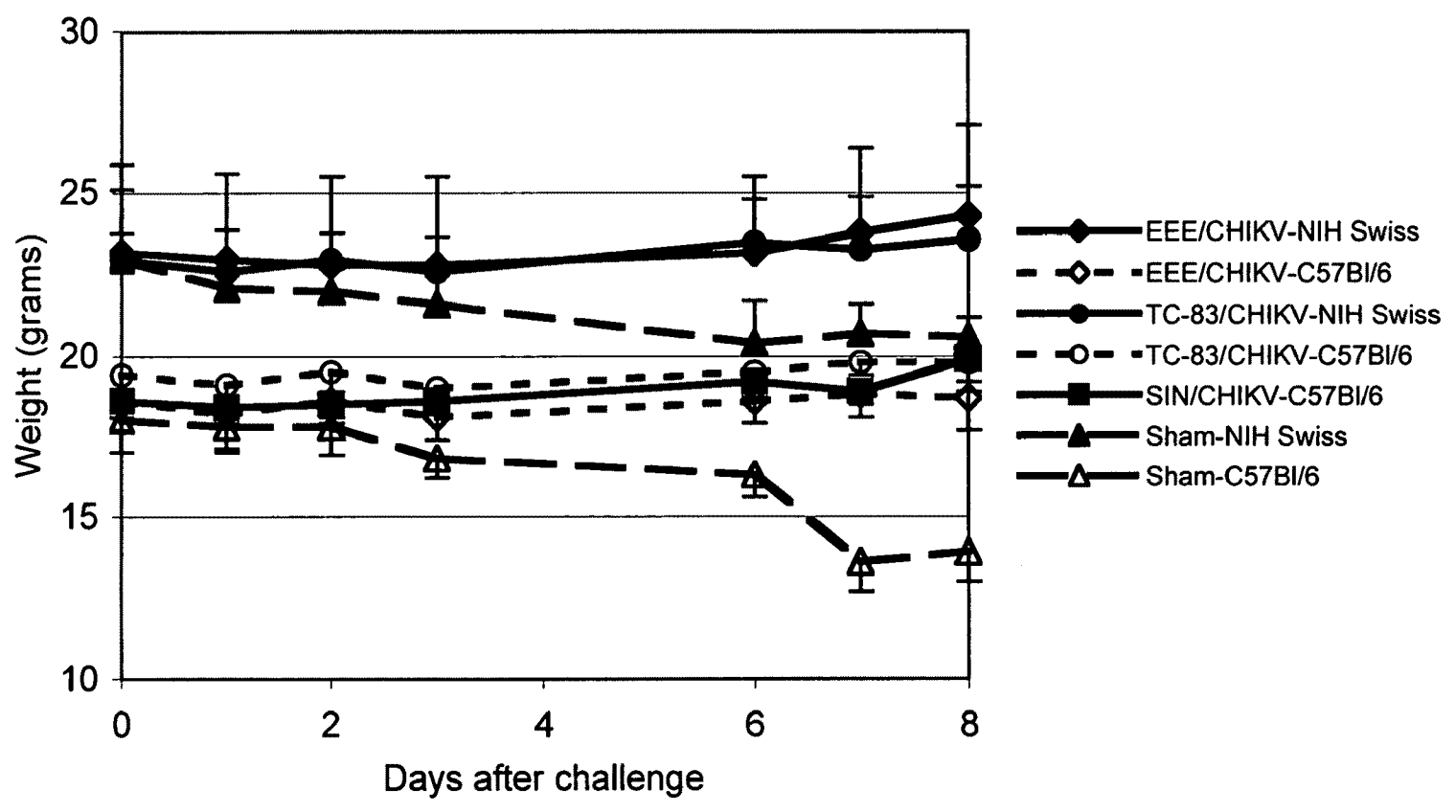

*IN challenge with 6.5 $\log_{10}$ PFU of the Ross CHIKV strain;
**PRNT$_{80}$ $\geq 20$ Protection Against CHIKV Challenge The vaccinated C57BL/6 mice described above were challenged IN with 6.5 $\log_{10}$ PFU of the Ross CHIKV strain 21 days after immunization. Vaccinated and sham-vaccinated NIH Swiss mice were divided into 2 groups; each group (5 per cohort) was challenged either IN with the Ross strain as described above, or IN with the LR strain at dose of 6.5 $\log_{10}$ PFU. All sham-vaccinated C57BL/6 mice produced viremia on days 1-2 after challenge (Table 9) and showed clinical signs by day 6, with ruffled hair, a hunched posture, inactivity and neurologic signs, as well as significant body weight losses (ANOVA, $p<0.001$) (FIG. 8). In contrast, all mice vaccinated with the chimeras were active and showed no signs of disease. Sham-vaccinated NIH Swiss mice exhibited some signs of disease after challenge with the Ross strain, including weight loss on days 7 and 8 (ANOVA, $p<0.05$ as compared to TC-83/CHIKV or EEE/CHIKV-vaccinated animals, see FIG. 8), and viremia during the first two days post-challenge (Table 9). Vaccinated NIH Swiss mice challenged with the LR strain also showed no significant body weight alterations, in contrast to sham-vaccinated animals.

TABLE 9

Viremia in vaccinated or sham-vaccinated mice after IN challenge with CHIKV*

| Mouse strain | Vaccine strain | Virus titer ($\log_{10}$ PFU/ml) ± SD | | |
|---|---|---|---|---|
| | | Day 1 | Day 2 | Day 3 |
| C57BL/6 | Sham | 2.5 ± 0.4 | 2.0 ± 0.0 | <0.9 |
| | EEE/CHIKV | <0.9 | <0.9 | <0.9 |
| | TC-83/CHIKV | <0.9 | <0.9 | <0.9 |
| | SIN/CHIKV | <0.9 | <0.9 | <0.9 |
| NIH Swiss | Sham | 3.3 ± 0.8 | 3.2 ± 0.7 | <0.9 |
| | EEE/CHIKV | <0.9 | <0.9 | <0.9 |
| | TC-83/CHIKV | <0.9 | <0.9 | <0.9 |
| | SIN/CHIK | <0.9 | <0.9 | <0.9 |

*IN challenge with 6.5 $\log_{10}$ PFU of the Ross CHIKV strain

Discussion

Recent massive epidemics of highly debilitating, chronic arthralgia in India and islands off the east coast of Africa have underscored the importance CHIKV as an emerging tropical arbovirus. Furthermore, the introduction of CHIKV into a temperate region of northern Italy, followed by autochthonous transmission there by *Ae. albopictus*, indicates the potential for CHIKV to become endemic in temperate areas of the Europe, North and South America, and Asia where this mosquito vector is established.

Currently, no effective therapy exists for treating patients suffering from CHIK, and prevention relies on mosquito control, which is largely ineffective for other tropical arboviruses like DENV that are transmitted by peridomestic vector mosquitoes in urban settings. A live CHIKV vaccine candidate developed by the U.S. Army, strain 181/25, is immunogenic in mice, rhesus macaques, and humans, but proved to be mildly reactogenic during phase II safety studies. Like other traditionally derived RNA virus vaccines that depend on small numbers of attenuating point mutations, attenuation of this vaccine is probably unstable and prone to reversion during replication in vaccinees.

The present invention developed an alternative approach to live alphavirus vaccines: chimeric viruses that are uniformly attenuated with no evidence of reactogenicity in murine models. The live virus vaccine approach was selected because it is the most practical for diseases of developing nations due to its low manufacturing cost and the rapid, long-term immunity that is usually generated. For example, the live-attenuated 17-D yellow fever virus vaccine is administered at a cost of only US$0.65 per person, and boosters are recommended only 10 years after the single initial dose.

Attenuation and Safety

Like previous chimeras that were developed as vaccines against VEE and EEE, 3 different CHIKV vaccine strains were attenuated in various mouse models compared to the parent viruses and other alphavirus vaccine strains. The chimeras also induced robust humoral immunity in vaccinated mice, with no detectable reactogenicity, even after relatively high doses of 5.3-5.8 $\log_{10}$ PFU. None of the adult or subadult mice infected exhibited any signs of neurologic disease, febrile responses, or growth delays as indicated by continued weight gain. Attenuation of the chimeric vaccine candidates appeared to be better than that of vaccine strain 181/25, which produced higher levels of viremia and replication in the joints of newborn mice. The joints are important sites of pathology in CHIKV-induced arthralgic disease, and strain 181/25 produced arthralgia in some vaccinees. Therefore, the finding that chimeric vaccine candidates replicate less efficiently in and/or around the joints of mice suggests that they may be less reactogenic in humans than strain 181/25.

Although the murine model for CHIK reproduced disease only in younger age groups, vaccination of 3-week-old mice with the chimeras, and IP or IN challenge 3 weeks later, demonstrated significant protection from weight loss as well as challenge virus replication in most organs and serum, measured at 2 different time points.

Immunogenicity

All of the chimeric vaccine candidates produced robust neutralizing Ab titers after a single SC inoculation of 5.3-5.8 $\log_{10}$ PFU. These doses were selected based on the titers of previously reported chimeric alphavirus vaccine candidates required to achieve uniformly robust immunity and protection against severe challenge. In the present study, the CHIKV chimera versions that used the attenuated VEEV strain TC-83 or naturally attenuated EEEV backbones were consistently more immunogenic in outbred or inbred mice than the chimera with a SINV backbone, as measured by mean neutralizing Ab titers, yet were not detectably more virulent. Both of these chimeras also appeared to be more immunogenic than vaccine strain 181/25 even though they produced lower viremia and replication in the joints of newborn mice.

Considering the natural attenuation of the SA EEEV strain BeAr436087 in mice, hamsters, guinea pigs and marmosets, the documented role of the nsPs of this strain in natural attenuation, and the epidemiological evidence that all South American EEEV strains are attenuated for humans, the EEE/CHIKV may be the most promising of the 2 vaccine candidates. Additional studies to determine if strain BeAr436087 is attenuated in other rodent models and equids would be useful to support the rationale for further development of this vaccine candidate.

The following references were cited herein:
Aguilar et al., *J Virol*, 2007, 8: 3866-3876.
Berge et al., *Am J Hyg*, 1961, 73: 209-218.
Bernard et al., *Virology*, 2000, 276: 93-103
Byrnes and Griffin *J Virol*, 1998, 72: 7349-7356.
Byrnes and Griffin *J Virol*, 2000, 74: 644-651.
Charrel et al., *N Engl J Med*, 2007, 356: 769-771.
Edelman et al., *Am J Trop Med Hyg*, 2000, 62: 681-685.
Frolova et al., *J Virol*, 2002, 76: 11254-11264.
Garmashova et al, *J Virol*, 2007, 81: 2472-2484.
Kalantri et al, *Natl Med J India*, 2006, 19: 315-322.
Kielian and Helenius, 1986. Entry of alphaviruses, p. 91-119. In Schlesinger et al. (ed), The Togaviruses and Flaviviruses. Plenum Press, New York.
Kinney et al., *J. Virol.*, 1993, 67: 1269-1277.
Klimstra et al., *J. Virol.*, 2003, 77: 12022-12032.

Klimstra et al., *J. Virol.*, 1998, 72: 7357-7366.
Kuhn et al., *J. Virol.*, 1996, 70: 7900-7909.
Kuhn et al., *J. Virol.*, 1992, 66: 7121-7127.
Levitt et al., *Vaccine*, 1986, 4: 157-162.
Ludwig et al., *J Virol*, 1996, 70: 5592-5599.
Pittman et al., *Vaccine.*, 1996, 14: 337-343.
Schlessinger et al., 1996. Togaviridae: The viruses and their replication, p. 825-842. In Fields, et al., Fields Virology, $3^{rd}$ Edn. Raven Press, New York.
Schuffenecker et al., *Plos Med.*, 2006, 3: e263.
Strauss and Strauss, *Microbiol Rev.*, 1994, 58: 491-562.
Tsai et al, 2002. Alphaviruses, p. 1177-1210. In D. D. Richman, R. J. Whitley, and F. G. Hayden (ed), Clinical Virology, ASM Press, Washington D.C.
U.S. Depart of Health and Human Services, 1999, Biosafety in Microbiological and Biomedical Labs, $4^{th}$ Edn, U.S. Govt Printing Office, Washington D.C.
Ubol and Griffin, *J. Virol.*, 1991, 65: 6913-6921.
Wang et al, *J. Virol.*, 1992, 66: 4992-5001.
Wang et al, *Virology*, 1991, 181: 694-702.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. An RNA encoding a chimeric alphavirus comprising
   (i) a Venezuelan equine encephalitis virus (VEEV) or an Eastern equine encephalitis virus (EEEV) backbone comprising cis-acting sequences from 5' and 3' termini, and nonstructural protein genes of VEEV or EEEV; and
   (ii) a structural protein-encoding segment comprising Chikungunya structural protein genes.

2. The RNA of claim 1, wherein the Chikungunya virus structural protein genes comprise the 5' untranslated region of the subgenomic RNA of Chikungunya virus.

3. The RNA of claim 1, wherein the Eastern equine encephalitis virus is BeAr436087, or FL93-939.

4. The RNA of claim 1, wherein the Venezuelan equine encephalitis virus is TC-83, 3908 or ZPC738.

5. An attenuated chimeric alphavirus comprising the RNA of claim 1.

6. A pharmaceutical composition comprising the attenuated chimeric alphavirus of claim 5 and a pharmaceutically acceptable carrier.

7. An immunogenic composition, comprising:
   a live attenuated chimeric alphavirus of claim 5.

8. A method of protecting an individual from infections resulting from exposure to Chikungunya virus, comprising:
   administering an effective amount of the attenuated chimeric alphavirus of claim 5, wherein said composition elicits a protective immune response against the Chikungunya virus in the individual.

9. The method of claim 8, wherein the chimeric alphavirus is inactivated.

10. A method of determining the presence of an antibody to Chikungunya virus in a subject, comprising:
    contacting a serum sample from the subject with a chimeric alphavirus of claim 5 and determining the presence or absence of antigenic reactivity to the Chikungunya virus in the serum sample, thereby determining the presence of antibody to Chikungunya virus in the subject.

11. The method of claim 10, wherein the assays are enzyme linked immunosorbent assays, hemagglutination inhibition assay, complement fixation assay or plaque reduction neutralization assay.

12. The method of claim 10, wherein the chimeric alphavirus is inactivated.

13. The method of claim 12, wherein the assays are enzyme linked immunosorbent assays, hemagglutination inhibition assay, complement fixation assay or plaque reduction neutralization assay.

14. A kit, comprising: the attenuated chimeric alphavirus of claim 5 and a detection reagent.

15. A DNA encoding the RNA of claim 1.

* * * * *